United States Patent
Shi et al.

(10) Patent No.: US 11,583,492 B2
(45) Date of Patent: Feb. 21, 2023

(54) ***MACADAMIA INTEGRIFOLIA* WHITENING EXTRACT AND PREPARATION METHOD THEREOF**

(71) Applicant: SOUTHWEST FORESTRY UNIVERSITY, Kunming (CN)

(72) Inventors: Rui Shi, Kunming (CN); Can Liu, Kunming (CN); Wenlin Wang, Kunming (CN); Liang Tao, Kunming (CN); Jinchao Qiao, Kunming (CN); Siqi Li, Kunming (CN); Na Lu, Kunming (CN)

(73) Assignee: SOUTHWEST FORESTRY UNIVERSITY, Kunming (CN)

( * ) Notice: Subject to any disclaimer, the term of this patent is extended or adjusted under 35 U.S.C. 154(b) by 0 days.

(21) Appl. No.: 17/662,275

(22) Filed: May 6, 2022

(65) Prior Publication Data
US 2022/0387296 A1    Dec. 8, 2022

(30) Foreign Application Priority Data
May 28, 2021   (CN) .......................... 202110593903.5

(51) Int. Cl.
*A61K 8/9789*   (2017.01)
*A61Q 19/02*    (2006.01)

(52) U.S. Cl.
CPC ............ *A61K 8/9789* (2017.08); *A61Q 19/02* (2013.01)

(58) Field of Classification Search
None
See application file for complete search history.

(56) References Cited

FOREIGN PATENT DOCUMENTS

CN              110760013 A    *   2/2020   ........... A23L 33/105

* cited by examiner

*Primary Examiner* — Nannette Holloman
(74) *Attorney, Agent, or Firm* — Culhane Meadows, PLLC.; Robert C. Klinger

(57) ABSTRACT

A *Macadamia integrifolia* whitening extract and a preparation method thereof are disclosed. The preparation method includes: S1: carrying out a hot extraction on a crushed *Macadamia integrifolia* green peel using an ethanol solution as an extraction solvent to obtain a crude green peel extract; then enzymatically treating the crude green peel extract using a snailase to obtain a enzymatic hydrolysate; finally extracting the enzymatic hydrolysate using a petroleum ether, and taking an aqueous phase to obtain a green peel extract; S2: carrying out a hot extraction on crushed Sichuan lovase rhizome decoction pieces using an ethanol solution as an extraction solvent to obtain a Sichuan lovase rhizome extract; S3: dispersing the green peel extract and the Sichuan lovase rhizome extract in water to obtain a whitening extract.

10 Claims, No Drawings

MACADAMIA INTEGRIFOLIA WHITENING EXTRACT AND PREPARATION METHOD THEREOF

CROSS REFERENCE TO RELATED APPLICATION

This patent application claims the benefit and priority of Chinese Patent Application No. 202110593903.5 filed on May 28, 2021, the disclosure of which is incorporated by reference herein in its entirety as part of the present application.

TECHNICAL FIELD

The present disclosure relates to the technical field of preparation of natural products, and specifically to a *Macadamia integrifolia* whitening extract and a preparation method thereof.

BACKGROUND ART

The *Macadamia integrifolia* green peel contains a lot of phenolic compounds, such as arbutin which has the functions of repairing sun damage and whitening. Green peel is the peel of *Macadamia integrifolia*, which accounts for more than 50% by weight of the fresh fruit. Although the green peel has a relatively large biomass, the resources of the *Macadamia integrifolia* green peel are not fully utilized. Most of the green peel is discarded and only a small part is used for fertilizer production. A large number of discarded green peels are accumulated, decayed and deteriorated in the natural environment, causing a severe environmental pollution. Therefore, the first step in the comprehensive utilization of *Macadamia integrifolia* resources is to realize the comprehensive utilization of its discarded ingredients. If the functional ingredients in the *Macadamia integrifolia* green peel can be fully developed, it is possible to improve the additional value of *Macadamia integrifolia* and thereby expand the *Macadamia integrifolia* industry chain. In the prior art, the refined products obtained by extracting and preparing from *Macadamia integrifolia* green peel have limited content of substances with a whitening effect such as arbutin, and thus the whitening effect thereof cannot meet application requirements. In addition, due to the complex composition of the phenolic substances in the green peel, a more complicated operation process is required to extract, separate and purify the target components, which increases the cost of recycling *Macadamia integrifolia* green peel. In addition, the existing extraction and separation technologies for the whitening components of *Macadamia integrifolia* green peel is not applicable for industrial production, which hinders the comprehensive utilization of resources of *Macadamia integrifolia* green peel. There is an urgent need to develop a low-cost, convenient and quick preparation method of whitening products from *Macadamia integrifolia* green peel to meet the needs of practical applications.

SUMMARY

The present disclosure intends to provide a method for preparing a *Macadamia integrifolia* whitening extract so as to solve the technical problem that the ingredients with a whitening effect in the *Macadamia integrifolia* green peel are not fully utilized.

To achieve the above object, the present disclosure employs the following technical solutions:

A method for preparing a *Macadamia integrifolia* whitening extract, comprising the following steps in sequence:

S1: carrying out a hot extraction on a crushed *Macadamia integrifolia* green peel by using an ethanol solution as an extraction solvent to obtain a crude green peel extract; then enzymatically treating the crude green peel extract by using a snailase to obtain an enzymatic hydrolysate; finally extracting the enzymatic hydrolysate by using a petroleum ether, and taking an aqueous phase to obtain a green peel extract;

S2: carrying out a hot extraction on crushed Sichuan lovase rhizome decoction pieces by using an ethanol solution as an extraction solvent to obtain a Sichuan lovase rhizome extract; and S3: dispersing the green peel extract and the Sichuan lovase rhizome extract in water to obtain a whitening extract.

This solution has the following principle and advantages: in this solution, the green peel extract and the Sichuan lovase rhizome extract are used in combination to prepare a whitening extract with tyrosinase inhibitory activity. Sichuan lovase rhizome is a common Chinese medicinal material, which is often used for promoting blood circulation and Qi circulation, relieving rheumatic pains, and has an effect of whitening and removing dark spots. The use of Sichuan lovase rhizome as a raw material for whitening products has been accepted by consumers. Sichuan lovase rhizome decoction pieces are medicinal materials obtained by removing impurities from the root of Sichuan lovase rhizome, washing, cutting into thick slices and drying said root. The arbutin in the *Macadamia integrifolia* green peel also has a certain whitening effect, but its whitening effect is limited. Therefore, the *Macadamia integrifolia*s green peel has not been fully utilized for now, and a large amount of it has been discarded, resulting in waste of resources and environmental pollution. The inventor used a Sichuan lovase rhizome extract and a *Macadamia integrifolia* extract in combination and found that the whitening effect by the combined use was significantly better than the two extracts alone. Therefore, the use of the two extracts for the development of related whitening products could not only reduce the consumption of Sichuan lovase rhizome (the price of Sichuan lovase rhizome is higher than the green peel, and thus a large-scale use of the Sichuan lovase rhizome will increase cost), but also make full use of the discarded Macadamia nut green peel. As such, the production cost would be reduced and meanwhile the comprehensive utilization of resources would be achieved, achieving two goals with one action.

The Sichuan lovase rhizome extract is prepared by a process including carrying out a hot extraction on crushed Sichuan lovase rhizome decoction pieces by using ethanol as an extraction solvent, so that the alcohol-soluble substances in Sichuan lovase rhizome are fully extracted, and the alcohol extract of Sichuan lovase rhizome contains a large number of phenolic acids with a whitening effect, such as ferulic acid, chlorogenic acid and caffeic acid.

The green peel extract is prepared by a process including carrying out a hot extraction on a crushed fresh *Macadamia integrifolia* green peel by using ethanol as an extraction solvent to obtain a crude green peel extract; subjecting the crude green peel extract to a snailase enzymatic hydrolysis to decompose impurities that affect the subsequent extraction and separation steps; and then extracting the resulting enzymatic hydrolysate with a petroleum ether several times, retaining an aqueous phase, and concentrating the aqueous phase to obtain the green peel extract, wherein the crude green peel extract contains a large number of alcohol-soluble substances, including arbutin, helicid and gastrodin, etc., and the snailase is a composite enzyme with more than 20 kinds of enzymes including cellulase, pectinase, amylase, protease, etc. The use of snailase could ensure the full decomposition of impurities. The green peel extract prepared by this process contains a certain amount of arbutin and other substances, and has a certain tyrosinase inhibitory activity, but the activity is not very ideal compared to the Sichuan lovase rhizome extract. However, the combined use of green peel extract and Sichuan lovase rhizome extract results in a more ideal whitening effect.

At the beginning of the research, the inventor intended to obtain a method for improving the whitening effect of a *Macadamia integrifolia* extract. After a large number of experimental studies, it was unexpectedly discovered that although the method in the present application could not directly improve the whitening effect of the green peel extract, the green peel extract of the present disclosure could be combined with existing whitening substances to play an auxiliary and synergistic effect. The solutions of the present disclosure could provide a feasible way for the comprehensive utilization of *Macadamia integrifolia* green peel resources, reduce the production cost of whitening products, and achieve the goal of environmental protection and energy saving.

In some embodiments, in S3, a mass ratio of the green peel extract to the Sichuan lovase rhizome extract is ranging from 1:4 to 4:1.

With the above technical solutions, the green peel extract could produce a more significant synergistic effect on the Sichuan lovase rhizome extract under the above ratio.

In some embodiments, a mass fraction of the green peel extract in the whitening extract is in the range of 2-8%.

By the above technical solution, the green peel extract with the above mass fraction has a more significant synergistic effect on the Sichuan lovase rhizome extract. Although the arbutin in the *Macadamia integrifolia* green peel has an effect of repairing sun damage and whitening, the direct whitening effect of the green peel extract prepared according to this extraction embodiment is not very obvious, which means that the content of arbutin in the green peel extract is not very high. The effect of green peel extract in this whitening extract is mainly to synergize Sichuan lovase rhizome extract, indicating that the green peel extract obtained according to this embodiment contains one or more components related to the tyrosinase inhibitory effect of Sichuan lovase rhizome extract.

In some embodiments, a mass fraction of the Sichuan lovase rhizome extract in the whitening extract is in the range of 2-8%.

By the above technical solution, the Sichuan lovase rhizome extract with the above-mentioned mass fraction could produce a better effect of inhibiting tyrosinase activity. Sichuan lovase rhizome contains ferulic acid, chlorogenic acid, caffeic acid and other ingredients, which have a good whitening effect.

In some embodiments, in S1, a volume fraction of the ethanol solution is 80%, and a ratio of the crushed *Macadamia integrifolia* green peel to the ethanol solution with the volume fraction of 80% is 1 kg:6 L.

By the above technical solution, the use of the above-mentioned amount and volume fraction of the ethanol solution results in realizing a full dissolution of functional components.

In some embodiments, in S1, the hot extraction is carried out at a temperature of 60° C. 2 times, with each time for 12 h.

By the above technical solution, the material is extracted twice under a hot extraction condition of 60° C., and thereby the effective components in *Macadamia integrifolia* green peel could be fully extracted.

In some embodiments, in S1, the crude green peel extract is dispersed in water, and a snailase is added to obtain an enzymatic hydrolysis solution, wherein a ratio of the crude green peel extract to water is 1 g:10 ml, and a mass fraction of the snailase in the enzymatic hydrolysis solution is 0.2%; the enzymatically treating is carried out at a temperature of 37° C. for 4 h.

By the above technical solution, snailase contains more than 20 kinds of enzymes such as cellulase, pectinase, amylase and protease, and thus the use of snailase could decompose the substances in the crude green peel extract that affect the separation of functional components. Experiments have proved that when a snailase is used and then petroleum ether is used for subsequent extraction, a large number of ingredients with synergistic effects on Sichuan lovase rhizome extract could be retained in the aqueous phase, and unnecessary components would enter the petroleum ether phase.

In some embodiments, in S1, the enzymatic hydrolysate is dispersed in water to obtain a dispersion, with a ratio of the enzymatic hydrolysate to water being 1 g:10 ml; the dispersion is then extracted 3 times with a petroleum ether, and the resulting aqueous phase is taken and concentrated to obtain a green peel extract.

By the above technical scheme, impurities could be removed effectively by a petroleum ether extraction, and the synergistic components in the green peel could be enriched.

In some embodiments, in S2, a volume fraction of the ethanol solution is 70%, and a ratio of the crushed Sichuan lovase rhizome decoction pieces to the ethanol solution with the volume fraction of 70% is 1 kg:8 L; the hot extraction is carried out at a temperature of 60° C. 2 times, with each time for 12 h.

By the above technical solution, with using 70% ethanol as the extraction solvent and hot extracting the powder of Sichuan lovase rhizome decoction pieces, the ingredients having a whitening effect such as phenolic acids in the Sichuan lovase rhizome could be fully extracted and dissolved.

The present disclosure further provides a whitening extract obtained by the method for preparing a *Macadamia integrifolia* whitening extract.

By the above technical solution, when using the green peel extract and the Sichuan lovase rhizome extract in combination, a more significant synergistic effect is produced, which could effectively inhibit tyrosinase activity, inhibit melanin production, and produce a good whitening effect.

DETAILED DESCRIPTION OF THE EMBODIMENTS

The present disclosure is further described in detail below by specific examples.

Example 1

Preparation of a Sichuan Lovase Rhizome Extract

Sichuan lovase rhizome decoction pieces were crushed, and screened through a 20-mesh sieve to obtain a Sichuan lovase rhizome powder. The Sichuan lovase rhizome powder was then put into an extraction tank, and an ethanol with a volume fraction of 70% (70% ethanol for short) was added into the extraction tank with an amount of 8 L 70% ethanol per kg of Sichuan lovase rhizome powder. The resulting mixture was subjected to a hot extraction at 60° C. for 12 hours while stirring slowly at a speed of 50-100 revolutions/min. After 12 h, the resulting material was filtered, and a first filtrate was retained. 70% ethanol was added into the residue with an amount of 8 L 70% ethanol per kg of Sichuan lovase rhizome powder again, and the residue was extracted at 60° C. for 12 h while stirring slowly at a speed of 50-100 revolutions/min. After 12 h, the resulting material was filtered, a second filtrate was retained, and the residue was discarded. The first filtrate and the second filtrate were combined to obtain an extraction solution. The extract solution was concentrated under reduced pressure (60° C.) to a paste shape to obtain the Sichuan lovase rhizome extract (with a density of 1.21 g/ml).

Preparation of a *Macadamia integrifolia* Green Peel Extract

A fresh *Macadamia integrifolia* green bark was washed, dried in the shade, crushed and then screened through a 20-mesh sieve to obtain a fresh green peel powder. The fresh green peel powder was put into an extraction tank, and an ethanol with a volume fraction of 80% (80% ethanol for short) was added to the fresh green peel powder with an amount of 6 L 80% ethanol per kg of the fresh green peel powder. The resulting mixture was extracted at 60° C. for 12 h while stirring slowly at a speed of 50-100 revolutions/min. After 12 h, the resulting material was filtered, and a first crude extraction solution was retained. 80% ethanol was added to the residue with an amount of 6 L 80% ethanol per kg of the fresh green peel powder again, and the residue was extracted at 60° C. for 12 h while stirring slowly at a speed of 50-100 revolutions/min. After 12 h, the resulting material was filtered, a second crude extraction solution was retained, and the residue was discarded. The first crude extraction solution and the second crude extraction solution were combined to obtain a crude green peel extraction solution. The crude green peel extraction solution was concentrated under reduced pressure (60° C.) to a paste shape to obtain a crude green peel extract (with a density of 1.06 g/ml).

Pure water was added to the crude green peel extract with an amount of 10 ml per g of the crude green peel extract, and the resulting material was stirred until the dispersion was complete. Then a snailase (CAS: 9032-75-1) was added thereto, and the mixture was subjected to an enzymatic hydrolysis reaction, to obtain an enzymatic hydrolysis solution. The mass fraction of the snailase in the enzymatic hydrolysis solution was 0.2%. The enzymatic hydrolysis reaction was carried out at a temperature of 37° C. for 4 h. After the enzymatic hydrolysis reaction was completed, the enzymatic hydrolysis solution was concentrated under reduced pressure (60° C.) to a paste shape, obtaining an enzymatic hydrolysate in the form of a paste (with a density of 1.13 g/ml).

The enzymatic hydrolysate was dispersed in pure water and stirred until the dispersion was complete. 10 ml of pure water was added for per g of enzymatic hydrolysate. A petroleum ether was then added for extraction at room temperature, with a volume ratio of the pure water to the petroleum ether being 1:1. The extraction was repeated 3 times. The petroleum ether phase was discarded, and the aqueous phase was retained to obtain a purified liquid. The purified liquid was concentrated under reduced pressure (60° C.) to a paste shape to obtain a green peel extract in the form of a paste (with a density of 1.07 g/ml).

The green peel extract and the Sichuan lovase rhizome extract were dispersed in pure water evenly to obtain a whitening extract. Wherein, the mass ratio of the green peel extract to the Sichuan lovase rhizome extract was 1:1, and the mass fraction of the solid matter (i.e. the green peel extract and the Sichuan lovase rhizome extract) in the pure water was 10%. Due to the high content of solid matter, in order to make the solid matter fully dispersed, the whitening extract was magnetically stirred until the material was dispersed in pure water. It is noted that when the whitening extract is used in follow-up experiments, the whitening extract needs to be stirred and resuspended before use to ensure that the effective ingredients are fully and evenly dispersed in the liquid phase.

Example 2

This example is basically the same as Example 1, except that in the whitening extract, the mass ratio of the green peel extract to the Sichuan lovase rhizome extract was 1:4, and the mass ratio of the solid matter (i.e the green peel extract and the Sichuan lovase rhizome extract) in pure water was 10%.

Example 3

This example is basically the same as Example 1, except that in the whitening extract, the mass ratio of the green peel extract to the Sichuan lovase rhizome extract was 4:1, and the mass ratio of solid matter (i.e. the green peel extract and the Sichuan lovase rhizome extract) in pure water was 10%.

Comparative Example 1

This comparative example was basically the same as Example 1, except that the preparation of a *Macadamia integrifolia* green peel extract did not include an enzymatic hydrolysis step. This example is specifically as follows:

A fresh *Macadamia integrifolia* green peel was washed, dried in the shade, crushed and screened through a 20-mesh sieve to obtain a fresh green peel powder. The fresh green peel powder was put into an extraction tank, and an 80% ethanol was added to the fresh green peel powder with an amount of 6 L 80% ethanol per kg of the fresh green peel powder. The resulting mixture was extracted at 60° C. for 12 h while stirring slowly in the extraction tank at a speed of 50-100 revolutions/min. After 12 h, the resulting material was filtered, and a first crude extraction solution was retained. 80% ethanol was added to the residue with an amount of 6 L 80% ethanol per kg of the fresh green peel powder again, and the residue was extracted at 60° C. for 12 h while stirring slowly at a speed of 50-100 revolutions/min. After 12 h, the material was filtered, a second crude extraction solution was retained, and the residue was discarded. The first crude extraction solution and the second crude extraction solution were combined to obtain a crude green peel extraction solution. The crude green peel extraction solution was concentrated under reduced pressure (60° C.) to a paste shape to obtain a crude green peel extract (with a density of 1.10 g/ml).

Pure water was added to the crude green peel extract with an amount of 10 ml per g of the crude green peel extract, and the material was stirred until the dispersion was complete. A petroleum ether was then added for extraction at room temperature, with a volume ratio of the pure water to the petroleum ether being 1:1. The extraction was repeated 3 times. The petroleum ether phase was discarded, and the aqueous phase was retained to obtain a purified liquid. The purified liquid was concentrated under reduced pressure (60° C.) to a paste shape to obtain a green peel extract in the form of a paste (with a density of 1.02 g/ml).

The green peel extract and the Sichuan lovase rhizome extract were dispersed into pure water evenly to obtain a whitening extract. Wherein, the mass ratio of the green peel extract to the Sichuan lovase rhizome extract was 1:1, and the mass fraction of the solid matter (i.e. the green peel extract and the Sichuan lovase rhizome extract) in the pure water was 10%.

Experimental Example 1: Whitening Activity Test

Tyrosinase, also known as polyphenol oxidase or catechol oxidase, is a key rate-limiting enzyme for melanin production. Catalyzing the hydroxylation of L-tyrosine to L-dopa is attributed to a monophenolic enzyme activity, and oxidizing L-dopa to dopaquinone is attributed to a diphenolase activity. Dopaquinone was transformed into melanin through a series of complex reactions. Dopaquinone is a colored substance that can be measured by an ultraviolet-visible spectrophotometer at 475 nm. In this experimental example, L-dopa was used as a substrate to determine the inhibitory effect of test samples on tyrosinase activity, thereby reflecting the whitening effect of test samples.

Test group 1: The whitening extract prepared in Example 1 was used as the test sample.

Test group 2: The whitening extract prepared in Example 2 was used as the test sample.

Test group 3: The whitening extract prepared in Example 3 was used as the test sample.

Test group 4: The green peel extract prepared in Example 1 was used to prepare the test sample. Specifically, the green peel extract was dispersed in pure water, with the mass fraction of the green peel extract being 2%, to obtain the test sample.

Test group 5: the green peel extract prepared in Example 1 was used to prepare the test sample. Specifically, the green peel extract was dispersed in pure water, with the mass fraction of the green peel extract being 5%, to obtain the test sample.

Test group 6: the green peel extract prepared in Example 1 was used to prepare the test sample. Specifically, the green peel extract was dispersed in pure water, with the mass fraction of the green peel extract being 8%, to obtain the test sample.

Test group 7: The Sichuan lovase rhizome extract prepared in Example 1 was used to prepare the test sample. Specifically, the Sichuan lovase rhizome extract was dispersed in pure water, with the mass fraction of the Sichuan lovase rhizome extract being 2%, to obtain the test sample.

Test group 8: The Sichuan lovase rhizome extract prepared in Example 1 was used to prepare the test sample. Specifically, the Sichuan lovase rhizome extract was dispersed in pure water, with the mass fraction of the Sichuan lovase rhizome extract being 5%, to obtain the test sample.

Test group 9: The Sichuan lovase rhizome extract prepared in Example 1 was used to prepare the test sample. Specifically, the Sichuan lovase rhizome extract was dispersed in pure water, with the mass fraction of the Sichuan lovase rhizome extract being 8%, to obtain the test sample.

Test group 10: The whitening extract prepared by the comparative example was used as the test sample.

Each test sample in groups 1-10, phosphate buffer (PBS), and L-dopa solution (0.5 mg/ml, prepared with PBS) were precisely drawn and mixed thoroughly, and reacted in a thermostat water bath at 30° C. for 10 minutes. Thereafter, 0.1 mL a tyrosinase solution (approximately 100 U/ml, prepared with PBS) was quickly added thereto. The mixture was reacted in a thermostat water bath at 30° C. for another 10 minutes, and then quickly transferred to a 96-well microplate reader plate, and absorbance was measured at 475 nm. The tyrosinase inhibition rate was calculated as follows: $(((A-D)-(C-B))/(A-D))\times 100\%$, where A refers to the absorbance value measured after mixing and reacting 0.2 ml of PBS, 0.1 ml of L-dopa solution and 0.1 ml of tyrosinase solution, B refers to the absorbance value measured after mixing and reacting 0.2 ml of PBS, 0.1 ml of L-dopa solution and 0.1 ml of the test sample, C refers to the absorbance value measured after mixing and reacting 0.1 ml of PBS, 0.1 ml of L-dopa solution, 0.1 ml of tyrosinase solution and 0.1 ml of the test sample, and D refers to the absorbance value measured after mixing 0.3 ml of PBS and 0.1 ml of L-dopa solution. The experimental results are shown in Table 1.

TABLE 1

Test results of tyrosine activity inhibition rate

| Test group | Tyrosine activity inhibition rate (%) | | | Average inhibition rate (average value ± variance) |
|---|---|---|---|---|
| | Test 1 | Test 2 | Test 3 | |
| 1 | 63.7 | 65.4 | 65.1 | 64.7 ± 0.7 |
| 2 | 72.3 | 75.3 | 77.4 | 75.0 ± 2.1 |
| 3 | 42.1 | 39.6 | 41.3 | 41.0 ± 1.0 |
| 4 | 5.2 | 3.6 | 2.4 | 3.7 ± 1.1 |
| 5 | 10.6 | 11.9 | 10.7 | 11.1 ± 0.6 |
| 6 | 14.8 | 12.7 | 14.4 | 14.0 ± 0.9 |
| 7 | 21.6 | 23.6 | 25.1 | 23.4 ± 1.4 |
| 8 | 41.5 | 40.6 | 42.9 | 41.7 ± 0.9 |
| 9 | 53.9 | 54.7 | 54.6 | 54.4 ± 0.4 |
| 10 | 45.6 | 46.3 | 47.5 | 46.5 ± 0.8 |

From the data in Table 1, it can be seen that the green peel extract and the Sichuan lovase rhizome extract have a synergistically enhanced effect on tyrosinase inhibition when used in combination in Examples 1-3, which could enhance the whitening effect of the product. Comparing test group 1, test group 5 and test group 8, it can be found that when the test sample contains 5% by mass of Sichuan lovase rhizome extract and no green peel extract (test group 8), the inhibition rate is 41.7%, indicating a certain tyrosine inhibition effect; when the test sample contains 5% by mass of green peel extract and no Sichuan lovase rhizome extract (test group 5), the inhibition rate is 11.1%, indicating a weak tyrosinase inhibitory effect; when the test sample contains 5% by mass of Sichuan lovase rhizome extract and 5% by mass of green peel extract (test group 1), the inhibition rate increases to 64.7%, which is greater than the sum of 41.7% and 11.1%. This indicates that the combined use of green peel extract and Sichuan lovase rhizome extract has achieved a synergistic effect. Similarly, comparing test group 2, test group 4 and test group 9, it can be found that the inhibition rate of 75.0% is greater than the sum of 54.4% and 3.7%; comparing test group 3, test group 6 and test group 7, it can be found that the inhibition rate of 41.0% is greater than the sum of 14.0% and 23.4%. This further illustrates a synergistic effect produced by the combined use of green peel extract and Sichuan lovase rhizome extract.

The inventor's research indicates that both Sichuan lovase rhizome extract and green peel extract have a certain whitening effect (inhibiting tyrosinase activity), and under the extraction conditions of the present solutions, the activity of Sichuan lovase rhizome extract is higher than that of green peel extract. In addition, the inventor further analyzed the reasons for the synergistic effect and believes that the Sichuan lovase rhizome extract could bind to tyrosinase to a certain extent and fine-tune the three-dimensional structure of tyrosinase, so that the efficiency of tyrosinase binding to substrate becomes poor, thereby reducing the activity of tyrosinase, and the green peel extract further strengthens the combination of Sichuan lovase rhizome extract and tyrosinase. In addition, the inventor also finds by research that the preparation method of the green peel extract has an effect on the function effect of the green peel extract. Using the preparation method of comparative example 1, the obtained green peel extract does not have a significant effect on the tyrosinase inhibitory activity of the Sichuan lovase rhizome extract. The inventor conducted an analysis and believes that after the crude extract is extracted, subjecting the extract to a snailase hydrolysis could remove impurities that affect the subsequent extraction process, so that the subsequent petroleum ether extraction process could enrich more effective substances, and thereby achieve the synergistic effect of green peel extract and Sichuan lovase rhizome extract better.

The above are merely the embodiments of the present disclosure, and common knowledge such as specific technical solutions and/or characteristics that are well-known in these solutions are not described here too much. It should be noted that for those skilled in the art, modifications and improvements could be made without departing from the technical solution of the present disclosure, which should also be regarded to be within the protection scope of the present disclosure and not affect the implementation effect and the practicality of the present disclosure. The scope of protection claimed in this application shall be defined by the content of the claims, and the specific implementation modes in the description could be used to interpret the content of the claims.

What is claimed is:

1. A method for preparing a *Macadamia integrifolia* whitening extract, the method comprising the following steps in sequence:
    S1: carrying out a hot extraction on a crushed *Macadamia integrifolia* green peel by using an ethanol solution as an extraction solvent to obtain a crude green peel extract; then enzymatically treating the crude green peel extract by using a snailase to obtain a enzymatic hydrolysate; finally extracting the enzymatic hydrolysate by using a petroleum ether, and taking an aqueous phase to obtain a green peel extract;
    S2: carrying out a hot extraction on crushed Sichuan lovase rhizome decoction pieces by using an ethanol solution as an extraction solvent to obtain a Sichuan lovase rhizome extract; and
    S3: dispersing the green peel extract and the Sichuan lovase rhizome extract in water to obtain a whitening extract.

2. The method of claim 1, wherein, in S3, a mass ratio of the green peel extract to the Sichuan lovase rhizome extract is ranging from 1:4 to 4:1.

3. The method of claim 2, wherein a mass fraction of the green peel extract in the whitening extract is in the range of 2-8%.

4. The method of claim 3, wherein a mass fraction of the Sichuan lovase rhizome extract in the whitening extract is in the range of 2-8%.

5. The method of claim 1, wherein, in S1, a volume fraction of the ethanol solution is 80%, and a ratio of the crushed *Macadamia integrifolia* green peel to the ethanol solution with the volume fraction of 80% is 1 kg:6 L.

6. The method of claim 5, wherein, in S1, the hot extraction is carried out at a temperature of 60° C. 2 times, with each time for 12 h.

7. The method of claim 1, wherein, in S1, the crude green peel extract is dispersed in water, and the snailase is added to obtain an enzymatic hydrolysis solution, wherein a ratio of the crude green peel extract to water is 1 g:10 ml, and a mass fraction of the snailase in the enzymatic hydrolysis solution is 0.2%; and
    the enzymatically treating is carried out at a temperature of 37° C. for 4 h.

8. The method of claim 1, wherein, in S1, the enzymatic hydrolysate is added in water to obtain a dispersion, wherein a ratio of the enzymatic hydrolysate to water is 1 g:10 ml; and then the dispersion is extracted 3 times by using the petroleum ether, and the aqueous phase is taken and concentrated to obtain the green peel extract.

9. The method of claim 1, wherein, in S2, a volume fraction of the ethanol solution is 70%, and a ratio of the crushed Sichuan lovase rhizome decoction pieces to the ethanol solution with the volume fraction of 70% is 1 kg:8 L; and
    the hot extraction is carried out at a temperature of 60° C. 2 times, with each time for 12 h.

10. A whitening extract obtained by the method of claim 9.

* * * * *